United States Patent [19]
Adam et al.

[11] Patent Number: 6,054,588
[45] Date of Patent: Apr. 25, 2000

[54] HETEROCYCLIC VINYL ETHERS

[75] Inventors: Geo Adam, Schopfheim; Sabine Kolczewski, Lörrach, both of Germany; Vincent Mutel, Mulhouse, France; Heinz Stadler, Rheinfelden, Switzerland; Jürgen Wichmann, Steinen; Thomas Johannes Woltering, Weil am Rhein, both of Germany

[73] Assignee: Hoffman-La Roche Inc., Nutley, N.J.

[21] Appl. No.: 09/304,624

[22] Filed: May 4, 1999

Related U.S. Application Data

[62] Division of application No. 09/121,737, Jul. 23, 1998.

[30] Foreign Application Priority Data

Aug. 14, 1997 [EP] European Pat. Off. ............... 97114065

[51] Int. Cl.$^7$ .................................................. C07D 257/04
[52] U.S. Cl. ............................................... 548/252
[58] Field of Search ............................................. 548/252

[56] References Cited

U.S. PATENT DOCUMENTS

| | | |
|---|---|---|
| 4,210,657 | 7/1980 | Zirngible et al. . |
| 4,330,545 | 5/1982 | Zirngible et al. . |
| 4,554,356 | 11/1985 | Zirngible et al. . |
| 4,764,526 | 8/1988 | Bockman et al. . |
| 5,658,943 | 8/1997 | Berryman et al. ...................... 514/466 |

FOREIGN PATENT DOCUMENTS

| | | |
|---|---|---|
| 90362/82 | 5/1983 | Australia . |
| 2839388 | 3/1980 | Denmark . |
| 3417468 | 11/1985 | Denmark . |
| 079856 | 5/1983 | European Pat. Off. . |
| WO 8202552 | 8/1982 | WIPO . |

OTHER PUBLICATIONS

Ann. N. Y. Acad. Sci. vol. 544, 1988, pp. 63–73.
Chem. Abstr. vol. 97, No. 19, 1982.
Neuropharmacology, vol. 36, No. 7, 1997, pp. 933–940.
Radul, et al. CA 124:86893 (1995).
Radul, et al. CA 116:128819 (1992).
Xie, et al., CA 109:129021 (1988).
Anon, CA 97:162901 (1982).

*Primary Examiner*—Patricia L. Morris
*Attorney, Agent, or Firm*—George W. Johnston; Patricia S. Rocha-Tramaloni; Robert A. Silverman

[57] ABSTRACT

The compounds of the formula

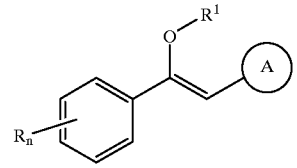

I wherein

R signifies halogen or lower alkyl;
n signifies 0–3;
R$^1$ signifies lower alkyl; cycloalkyl; benzyl optionally substituted by hydroxy, halogen, lower alkoxy or lower alkyl; benzoyl optionally substituted by amino, lower alkyl-amino or di-lower alkylamino; acetyl or cycloalkyl-carbonyl; and

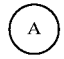

signifies an aromatic 5-membered residue which is bonded via a N-atom and which contains further 1–3 N atoms in addition to the linking N atom, as well as their pharmaceutically acceptable salts as therapeutically active substances, especially for the control or prevention of acute and/or chronic neurological disorders.

5 Claims, No Drawings

HETEROCYCLIC VINYL ETHERS

CROSS REFERENCE TO RELATED APPLICATION

This is a divisional of copending application Ser. No. 09/121,737 filed on Jul. 23, 1998.

BACKGROUND

In the central nervous system (CNS) the transmission of stimuli takes place by the interaction of a neurotransmitter, which is sent out by a neuron, with a neuroreceptor.

L-Glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

The ligands of the metabotropic glutamate receptors belonging to the second group are useful for treating Alzheimer's disease.

Other treatable indications in this connection are, Huntington's chorea, amyotrophic lateral sclerosis (ALS), dementia caused by AIDS, eye injuries, retinopathy, cognitive disorders, idiopathic parkinsonism or parkinsonism caused by medicaments as well as conditions which lead to glutamate-deficiency functions, such as for example muscle spasms, convulsions, migraine, urinary incontinence, nicotine addiction, psychoses, opiate addiction, anxiety, vomiting, chronic pain, dyskinesia, depressions and pains.

The ligands can also be used for the treatment or prevention of acute and/or chronic neurological disorders such as restricted brain function caused by bypass operations or transplants, poor blood supply to the brain, spinal cord injuries, head injuries, hypoxia caused by pregnancy, cardiac arrest and hypoglycaemia.

Objects of the present invention are the use of compounds of formula I and of their pharmaceutically acceptable salts as therapeutically active substances, as well as medicaments based on these compounds and their production, and novel compounds of formula I and their pharmacuetically acceptable salts per se and as pharmaceutically active substances for the control or prevention of illnesses of the aforementioned kind.

BRIEF SUMMARY OF THE INVENTION

In one aspect, the invention relates to a compound of the formula

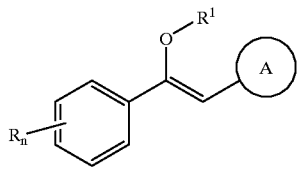

wherein

R is halogen or lower alkyl;

n is 0–3;

$R^1$ is lower alkyl; cycloalkyl; benzyl unsubstituted or substituted by hydroxy, halogen, lower alkoxy or lower alkyl; benzoyl unsubstituted or substituted by amino, lower alkylamino or di-lower alkylamino; acetyl or cycloalkyl-carbonyl; and

is an aromatic 5-membered residue which is bonded via a N-atom and which contains further 1 or 3 N atoms in addition to the linking N atom, or a pharmaceutically acceptable salt thereof.

In another aspect, the invention relates to a compound of the formula

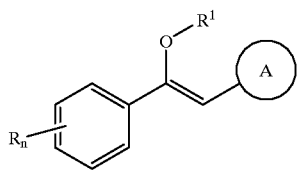

wherein

R is halogen or lower alkyl;

n is 0–3

$R^1$ is cycloalkyl; and

is an aromatic 5-membered residue which is bonded via a N atom and which contains further 3 N atoms in addition to the linking N atom, or a pharmaceutically acceptable salt thereof.

In another aspect, the invention relates to a pharmaceutical composition comprising (a) a compound of the formula I

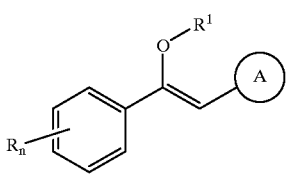

wherein
R is halogen or lower alkyl;
n is 0–3;
R¹ is lower alkyl; cycloalkyl; benzyl unsubstituted or substituted by hydroxy, halogen, lower alkoxy or lower alkyl; benzoyl unsubstituted or substituted by amino, lower alkylamino or di-lower alkylamino; acetyl or cycloalkyl-carbonyl; and

is an aromatic 5-membered residue which is bonded via a N-atom and which contains further 1–3 N atoms in addition to the linking N atom,
or a pharmaceutically acceptable salts as thereof, and
(b) a pharmaceutically inert carrier.

DETAILED DESCRIPTION OF THE INVENTION

The invention is concerned with heterocyclic vinyl ethers of the formula

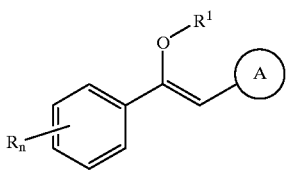

wherein
R is halogen or lower alkyl;
n is 0–3;
R¹ is lower alkyl; cycloalkyl; benzyl unsubstituted or substituted by hydroxy, halogen, lower alkoxy or lower alkyl; benzoyl unsubstituted or substituted by amino, lower alkylamino or di-lower alkylamino; acetyl or cycloalkyl-carbonyl; and

is an aromatic 5-membered residue which is bonded via a N-atom and which contains further 1–3 N atoms in addition to the linking N atom,
as well as their pharmaceutically acceptable salts.

Some triazole derivatives which fall under formula I have been known for a long time. They are described in European Application No. 079 856 for use as active substances for agrochemical pest control, preferably for the control or prevention of an attack by microorganisms.

It has surprisingly been found that the compounds of formula I are metabotropic glutamate receptor antagonists.

Novel compounds of formula I are especially those in which R and R¹ have the significance given above and

signifies an aromatic 5-membered ring which is bonded via a N atom and which contains further 1 or 3 N atoms in addition to the linking N atom or wherein R has the significance given above,

signifies an aromatic 5-membered ring which is bonded via a N atom and which contains a further 1–3 N atoms in addition to the linking N atom and R¹ signifies cycloalkyl.

The term "lower alkyl" used in the present description denotes straight-chain or branched saturated hydrocarbon residues with 1–7 carbon atoms, preferably with 1–4 carbon atoms, such as methyl, ethyl, n-propyl, i-propyl and the like.

The term "cycloalkyl" denotes cyclic saturated hydrocarbon residues with 3–7 carbon atoms in the ring, such as, for example, cyclopropyl, cyclobutyl, cyclopentyl, cyclohexyl and the like.

The term "lower alkoxy" denotes lower alkyl residues in the sense of the foregoing definition which are bonded via an oxygen atom.

The term "halogen" embraces fluorine, chlorine, bromine and iodine.

In the scope of the present invention those compounds of formula I in which R signifies chlorine, n is 1 or 2, R¹ signifies lower alkyl, cyclohexyl or benzyl and

signifies an aromatic 5-membered ring which is bonded via a N atom and which contains further 2 or 3 N atoms in addition to the linking N atom are preferred for use as therapeutically active substances.

The following are examples of preferred compounds of formula I:

1-[2-(2,4-dichloro-phenyl)-2-cyclohexyloxy-vinyl]-1H[1,2,4]triazole,
1-[2-(2,4-dichloro-phenyl)-2-benzyloxy-vinyl]-1H-tetrazole,
2-[2-(4-chloro-phenyl)-2-butoxy-vinyl]-2H-tetrazole,
1-[2-(4-chloro-phenyl)-2-butoxy-vinyl]-1H-[1,2,4]-triazole and
1-[2-(2,6-dichloro-phenyl)-2-butoxy-vinyl]-1H-[1,2,4]triazole.

The novel compounds of formula I can be manufactured by alkylating or acylating a compound of the formula

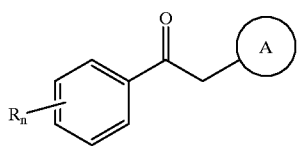

wherein R, n and

have the significances given earlier, and, if desired, converting a compound of formula I obtained into a pharmaceutically acceptable salt.

If desired, a functional group in a compound of formula I can be converted into a different functional group; in particular, amino groups can be alkylated to lower alkylamino or di-lower alkylamino groups or hydroxy groups can be alkylated. These procedures will be familiar to any person skilled in the art.

In the alkylation or acylation an acetophenone derivative of formula II is reacted with a suitable alkylating or acylating agent, preferably with benzyl bromide, benzoyl chloride, acetyl chloride, cyclohexyl triflate, cyclopropyl chloride, isopropyl bromide, n-butyl bromide, 4-methoxybenzyl chloride, isopropyl triflate, 4-dimethylaminobenzoyl chloride, benzyl chloride or the like. This reaction is effected according to known methods, preferably in the presence of sodium hydride. THF (tetrahydrofuran) and DMPU (1,3-dimethyl-3,4,5,6-tetrahydro-2(1H)-pyrimidinone) in the ratio 3:1 is especially suitable as the solvent.

This manufacturing variant is described in detail in Example I b).

The pharmaceutically usable salts can be produced readily according to known methods having regard to the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically usable salts of basic compounds of formula I. Compounds which contain the alkali or alkaline earth metals, for example sodium, potassium, calcium, magnesium or the like, basic amines or basic amino acids are suitable for the formation of pharmaceutically usable salts of acidic compounds.

The following Scheme 1 illustrates the manufacture of the compounds of formula I in overview, starting from the known compounds of formulae III and IV.

Scheme 1

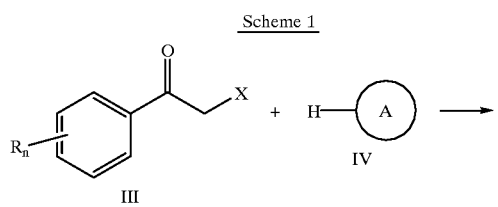

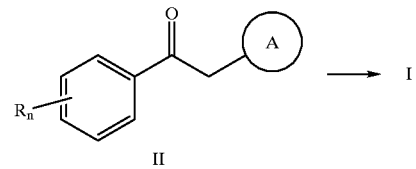

In this Scheme, R, n and

have the significances described above, X signifies halogen, preferably chlorine or bromine. A compound of formula IV can preferably be a triazole, tetrazole or imidazole of the general formulae

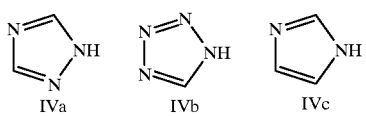

The compounds of general formulae II, III and IV are known or can be prepared according to known methods.

The following Table 1 shows a selection of tested compounds for use as therapeutically active substances in a mGluR affinity test (see p. 9):

| Compound No./Example No. | R | R1 | A |
|---|---|---|---|
| A | 2,4-Cl | i-Prop | triazole |
| B | 2,4-Cl | i-Bu | triazole |
| C | 2,4-Cl | n-Bu | triazole |
| D | 2,4,6-Cl | i-Prop | triazole |
| E | 2,4-Cl | CH₃ | triazole |
| F | 4-Br | n-Bu | triazole |

-continued

| Compound No./Example No. | R | R1 | —A |
|---|---|---|---|
| G | 2,4-F | i-Prop |  |
| H | 4-F | i-Prop |  |
| I | H | i-Prop |  |
| J | 4-Cl | n-Bu |  |
| K | 2,6-Cl | n-Bu |  |
| L/1 | 2,4-Cl | Benzyl |  |
| M/2 | 2,4-Cl | Benzoyl |  |
| N/3 | 2,4-Cl | Acetyl |  |
| O/4 | 2,4-Cl | Cyclohexyl |  |
| P/5 | 2,4-Cl |  |  |
| Q/6 | 4-CH₃ | i-Prop |  |
| R/7 | 2,6-Cl | Benzyl |  |
| S/8 | 2,4-Cl | n-Bu |  |

-continued

| Compound No./Example No. | R | R1 | —A |
|---|---|---|---|
| T/9 | 4-Cl | n-Bu |  |
| U/10 | 2,6-Cl | i-Prop |  |
| V/11 | 2,4-Cl | 4-Methoxy-benzyl |  |
| W/12 | 2,4-Cl | Benzoyl |  |
| X/13 | 2,4-Cl | i-Prop |  |
| Y/14 | 2,4-Cl | 4-Dimethylamino-benzyl |  |
| Z/15 | 2,4-Cl | Benzyl |  |
| AA/16 | 2,4-Cl | i-Prop |  |
| BB/17 | 2,4-Cl | n-Bu |  |

A  1-[2-(2,4-Dichloro-phenyl)-2-isopropoxy-vinyl]-1H-[1,2,4]triazole
B  1-[2-(2,4-Dichloro-phenyl)-2-isobutoxy-vinyl]-1H-[1,2,4]triazole
C  1-[-2-(2,4-Dichloro-phenyl)-2-butoxy-2-vinyl]-1H-[1,2,4]triazole
D  1-[2-(2,4,6-Trichloro-phenyl)-2-isopropoxy-vinyl]-1H-[1,2,4]triazole
E  1-[2-(2,4-Dichloro-phenyl)-2-methoxy-vinyl]-1H-[1,2,4]triazole
F  1-[2-(4-Bromo-phenyl)-2-butoxy-vinyl]-1H-[1,2,4]triazole
G  1-[2-(2,4-Difluoro-phenyl)-2-isopropoxy-vinyl]-1H-[1,2,4]triazole
H  1-[2-(4-Fluoro-phenyl)-2-isopropoxy-vinyl]-1H-[1,2,4]triazole
I  1-[2-(Phenyl)-2-isopropoxy-vinyl)-1H-[1,2,4]triazole
J  1-[2-(4-Chloro-phenyl)-2-butoxy-vinyl]-1H-[1,2,4]triazole
K  1-[2-(2,6-Dichloro-phenyl)-2-butoxy-vinyl]-1H-[1,2,4]triazole L  1-[2-(2,4-Dichloro-phenyl)-2-benzyloxy-vinyl]-1H-[1,2,4]triazole
M  1-(2,4-Dichloro-phenyl)-2-[1,2,4]triazol-1-yl-vinyl-benzoic acid ester
N  1-(2,4-Dichloro-phenyl)-2-[1,2,4]triazol-1-yl-vinyl-acetic acid ester
O  1-[2-(2,4-Dichloro-phenyl)-2-cyclohexyloxy-vinyl]-1H-[1,2,4]triazole
P  1-(2,4-Dichloro-phenyl)-2-[1,2,4]triazol-1-yl-vinyl-cyclopropane carboxylic acid ester
Q  1-[2-(4-Tolyl)-2-isopropoxy-vinyl]-1H-[1,2,4]triazole
R  1-[2-(2,6-Dichloro-phenyl)-2-benzyloxy-vinyl]-2H-tetrazole
S  2-[2-(2,4-Dichloro-phenyl)-2-butoxy-vinyl]-2H-tetrazole
T  2-[2-(4-Chloro-phenyl)-2-butoxy-vinyl]-2H-[1,2,4]tetrazole
U  2-[2-(2,4-Dichloro-phenyl)-2-isopropoxy-vinyl]-2H-tetrazole
V  2-[2-(2,4-Dichloro-phenyl)-2-(4-methoxy-benzyloxy)-vinyl]-2H-tetrazole
W  1-(2,4-Dichloro-phenyl)-2-tetrazol-1-yl-vinyl-benzoic acid ester
X  1-[2-(2,4-Dichloro-phenyl)-2-isopropoxy-vinyl]-1H-tetrazole
Y  1-(2,4-Dichloro-phenyl)-2-terazol-1-yl-vinyl-4-dimethylaminobenzoic acid ester
Z  1-[2-(2,4-Dichloro-phenyl)-2-benzyloxy-vinyl]-1H-tetrazole
AA  1-[2-(2,4-Dichloro-phenyl)-2-isopropoxy-vinyl]-1H-imidazole
BB  1-[2-(2,4-Dichloro-phenyl)-2-butoxy-vinyl]-1H-imidazole As mentioned above, the compounds of formula I and their pharmaceutically acceptable salts are metabotropic glutamate receptor antagonists and are useful for the treatment of Alzheimer's disease.

The binding of the compounds of formula I in accordance with the invention to group II metabotropic glutamate receptors was determined in vitro. The preparations were tested in accordance with the test given hereinafter:

The GTP $\gamma^{35}$S test was used to determine the affinity of a compound to the group II mGluR. Membranes which adhere to the rat mGluR2 receptor were used. These were stimulated with 10 $\mu$M 1S,3R-ACPD.

The Ki values of the compounds to be tested are given. The Ki value is defined by the following formula $$K_i = \frac{IC_{50}}{1 + \frac{[L]}{EC_{50}}}$$

in which the $IC_{50}$ values are those concentrations of the compounds to be tested in $\mu$M by which 50% of the effect of 1S,3R-ACPD are antagonized. [L] is the concentration of 1S,3R-ACPD and the $EC_{50}$ value is the concentration of 1S,3R-ACPD in nM which brings about 50% stimulation.

TABLE 2

| Activity on mGluR | |
|---|---|
| Compound No./Example No. | $K_i$ [$\mu$M] m-GluR2 |
| A | 1.17 |
| B | 0.64 |
| C | 1.40 |
| D | 2.70 |

TABLE 2-continued

| Activity on mGluR | |
|---|---|
| Compound No./Example No. | $K_i$ [$\mu$M] m-GluR2 |
| E | 11.00 |
| F | 0.66 |
| G | 7.60 |
| H | 10.00 |
| I | 12.70 |
| J | 0.60 |
| K | 0.60 |
| L/1 | 0.43 |
| M/2 | 1.20 |
| N/3 | 4.70 |
| O/4 | 0.10 |
| P/5 | 2.40 |
| Q/6 | 6.10 |
| R/7 | 2.00 |
| S/8 | 1.00 |
| T/9 | 0.32 |
| U/10 | 2.00 |
| V/11 | 1.00 |
| W/12 | 0.90 |
| X/13 | 1.30 |
| Y/14 | 1.40 |
| Z/15 | 0.27 |
| AA/16 | 7.71 |
| BB/17 | 4.30 |

The compounds of formula I and pharmaceutically acceptable salts thereof can be used as medicaments, for example in the form of pharmaceutical preparations. The pharmaceutical preparations can be administered orally, for example in the form of tablets, coated tablets, dragées, hard and soft gelatine capsules, solutions, emulsions or suspensions. However, the administration can also be effected rectally, for example in the form in suppositories, or parenterally, for example in the form of injections solutions.

The compounds of formula I and pharmaceutically acceptable salts thereof can be processed with pharmaceutically inert, inorganic or organic carriers for the production of pharmaceutical preparations. Lactose, corn starch or derivative thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, generally required in the case of soft gelatine capsules. Water, polyols, sucrose, invert sugar, glucose and the like are, for example, suitable carriers for the production of solutions and syrups. Adjuvants such as alcohols, polyols, glycerol, vegetable oils and the like can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, furthermore also a process for the production of such medicaments, which is characterised by bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01–20 mg/kg/day, with a dosage of 0.1–10 mg/kg/day being preferred for all of the indications described. The daily dosage for an adult human being of 70 kg body weight accordingly lies between 0.7–1400 mg per day, preferably between 7 and 700 mg per day.

The following Examples are intended to illustrate the manufacture of the specific novel compounds in more detail.

EXAMPLE 1

1-[2-2-(2,4-Dichloro-phenyl)-vinyl]-2-benzyloxy-1H-[1,2,4]triazole a) 10 g (44.8 mmol) of 2,2',4'-trichloroacetophenone were added portionwise at room temperature to a solution of 9.3 g (134 mmol) of triazole in 50 ml of dimethylformamide and stirred at 80° C. for 16 hours. The reaction mixture was added to 100 ml of 2N sodium hydroxide solution and extracted three times with 100 ml of ethyl acetate each time. The combined organic phases were dried over magnesium sulphate and concentrated in a vacuum. The crude product was purified by column chromatography on silica gel (ethyl acetate/methanol 100:5). 2.8 g (25%) of 1-(2,4-dichlorophenyl)-2-[1,2,4]triazol-1-yl-ethanone were obtained as a yellow-brown solid.

b) 670 mg (2.62 mmol) of 1-(2,4-dichlorophenyl)-2-[1,2,4]triazol-1-yl-ethanone in 12 ml of tetrahydrofuran and 4 ml of 1,3-dimethyl-3,4,5,6-tetrahydro-2(1H)-pyrimidinone were added to a suspension of 171 mg (3.92 mmol) of sodium hydride (55% in mineral oil) in 15 ml of tetrahydrofuran and 5 ml of 1,3-dimethyl-3,4,5,6-tetrahydro-2(1H)-pyrimidinone (DMPU) and stirred at room temperature for 3 hours. Thereafter, 396 mg (5.24 mmol) of benzyl bromide were added and the mixture was stirred at room temperature for a further 16 hours. The tetrahydrofuran was removed under a vacuum, the residue was added to 50 ml of water and extracted three times with 50 ml of diethyl ether each time. The combined organic phases were dried over magnesium sulphate and the diethyl ether was removed in a vacuum. The crude product was purified by column chromatography on silica gel (diethyl ether/pentane 1:4). In addition to mixed fractions with the C-alkylation product there were obtained 65 mg (7%) of pure 1-[2-(2,4-dichloro-phenyl)-2-benzyloxy-vinyl]-1H-[1,2,4]triazole as a colourless oil. [M+H]$^+$=345, 347.

EXAMPLE 2

1-(2,4-Dichloro-phenyl)-2-[1,2,4]triazole-1-vinyl-benzoic acid ester

Analogously to Example 1a,b, after reacting 1-(2,4-dichlorophenyl)-2-[1,2,4]triazol-1-yl-ethanone with benzoyl chloride there was obtained pure 1-(2,4-dichloro-phenyl)-2-[1,2,4]triazole-1-vinyl-benzoic acid ester. After reaction with oxalic acid there was obtained a salt of the composition $C_{17}H_{11}N_3O_2Cl_2.2C_2H_2O_4$ with a melting point of 130° C.

EXAMPLE 3

1-(2,4-Dichloro-phenyl)-2-[1,2,4]triazol-1-yl-vinyl-acetic acid ester

Analogously to Example 1a,b, after reacting 1-(2,4-dichlorophenyl)-2-[1,2,4]triazol-1-yl-ethanone with acetyl chloride there was obtained 1-(2,4-dichloro-phenyl)-2-[1,2,4]triazol-1-yl-vinyl-acetic acid ester as a white solid with m.p. 127° C.

EXAMPLE 4

1-[2-(2,4-Dichloro-phenyl)-2-cyclohexyloxy-vinyl]-1H-[1,2,4]triazole

Analogously to Example 1a,b, after reacting 1-(2,4-dichlorophenyl)-2-[1,2,4]triazol-1-yl-ethanone with cyclohexyl triflate there was obtained 1-[2-(2,4-dichloro-phenyl)-1-cyclohexyloxy-vinyl]-1H-[1,2,4]triazole as a white solid with m.p. 84° C.

EXAMPLE 5

1-(2,4-Dichloro-phenyl)-2-[1,2,4]triazol-1-yl-vinyl-cyclopropanecarboxylic acid ester Analogously to Example 1a,b, after reacting 1-(2,4-dichlorophenyl)-2-[1,2,4]triazol-1-yl-ethanone with cyclopropoyl chloride there was obtained 1-(2,4-dichloro-phenyl)-2-[1,2,4]triazol-1-yl-vinyl-cyclopropanecarboxylic acid ester as a white solid with m.p 108° C.

EXAMPLE 6

1-[2-(4-Tolyl)-2-isopropoxy-vinyl]-1H-[1,2,4]triazole

Analogously to Example 1a,b, after reacting 1-(4-methylphenyl)-2-[1,2,4]triazol-1-yl-ethanone with isopropyl bromide there was obtained 1-[2-(4-tolyl)-2-isopropoxy-vinyl]-1H-[1,2,4]triazole. After reaction with HCl in dioxan there was obtained a salt of the composition $C_{14}H_{17}N_3O.HCl.[M+H]^+$=243.

EXAMPLE 7

1-[2-(2,6-Dichloro-phenyl)-2-benzyloxy-vinyl]-1H-[1,2,4]triazole

Analogously to Example 1a,b, after reacting 1-(2,6-dichlorophenyl)-2-[1,2,4]triazol-1-yl-ethanone with benzyl chloride there was obtained 1-[2-(2,6-dichloro-phenyl)-2-benzyloxy-vinyl]-1H-[1,2,4]triazole. After reaction with oxalic acid there was obtained a salt with the composition $C_{17}H_{13}N_3OCl_2.C_2H_2O_4$, which decomposed at >71° C.

EXAMPLE 8

2-[2-(2,4-Dichloro-phenyl)-2-butoxy-vinyl]-2H-[1,2,4]tetrazole a) A solution of 15.9 g (71 mmol) of 2,2',4'-trichloroacetophenone in 100 ml of methylene chloride was slowly added dropwise while cooling with ice to a solution of 4.98 g (71 mmol) of tetrazole and 14.4 g (142 mmol) of triethylamine in 100 ml of methylene chloride and heated under reflux for 16 hours. The reaction mixture was added to 100 ml of water and extracted three times with 100 ml of methylene chloride each time. The combined organic phases were dried over magnesium sulphate and concentrated in a vacuum. The crude product was purified by column chromatography on silica gel (ethyl acetate/hexane 1:1). There were obtained 4.75 g (26%) of 1-(2,4-dichloro)-2-tetrazol-1-yl-ethanone and 7.80 g (43%) of 1-(2,4-dichlorophenyl)-2-tetrazol-2-yl-ethanone.

b) Analogously to Example 1b, after reacting 1-(2,4-dichlorophenyl)-2-tetrazol-2-yl-ethanone with n-butyl bromide there was obtained 2-[2-(2,4-dichloro-phenyl)-2-butoxzy-vinyl]-2H-[1,2,4]tetrazole as a colourless oil. [M+H]$^+$=313.

EXAMPLE 9

2-[2-(4-Chloro-phenyl)-2-butoxy-vinyl]-2H-[1,2,4] tetrazole

Analogously to Example 7a,b, after reacting 1-(4-chlorophenyl)-2-tetrazol-2-yl-ethanone with n-butyl bromide there was obtained 2-[2-(4-chloro-phenyl)-2-butoxy-vinyl]-2H-tetrazole as a colourless oil. [M+H]$^+$=279.

EXAMPLE 10

2-[2-(2,4-Dichloro-phenyl)-2-isopropoxy-vinyl]-2H-tetrazole

Analogously to Example 7a,b, after reacting 1-(2,4-dichlorophenyl)-2-tetrazol-2-yl-ethanone with isopropyl bromide there was obtained 2-[2-(2,4-dichloro-phenyl)-2-isopropoxy-vinyl]-2H-tetrazole as a colourless oil. [M]$^+$=299.

EXAMPLE 11

2-[2-(2,4-Dichloro-phenyl)-2-(4-methoxy-benzyloxy)-vinyl]-2H-tetrazole

Analogously to Example 7a,b, after reacting 1-(2,4-dichlorophenyl)-2-tetrazol-2-yl-ethanone with 4-methoxybenzyl chloride there was obtained 2-[2-(2,4-dichloro-phenyl)-2-(4-methoxy-benzyloxy)-vinyl]-2H-tetrazole as a colourless oil. [M+H]$^+$=376.

EXAMPLE 12

1-(2,4-Dichloro-phenyl)-2-tetrazol-1-yl-vinyl-benzoic acid ester

Analogously to Example 7a,b, after reacting 1-(2,4-dichlorophenyl)-2-tetrazol-1-yl-ethanone with benzoyl chloride there was obtained 1-(2,4-dichloro-phenyl)-2-tetrazol-1-yl-vinyl-benzoic acid ester as a colourless oil. [M]$^+$=360.

EXAMPLE 13

1-[2-(2,4-Dichloro-phenyl)-2-isopropoxy-vinyl]-1H-tetrazole

Analogously to Example 7a,b, after reacting 1-(2,4-dichlorophenyl)-2-tetrazol-1-yl-ethanone with isopropyl triflate there was obtained 1-[2-(2,4-dichloro-phenyl)-2-isopropoxy-vinyl]-1H-tetrazole as a white powder with m.p. 82° C.

EXAMPLE 14

1-(2,4-Dichloro-phenyl)-2-tetrazol-1-yl-vinyl-4-dimethylamino-benzoic acid ester Analogously to Example 7a,b, after reacting 1-(2,4-dichlorophenyl)-2-tetrazol-1-yl-ethanone with 4-dimethylamino-benzoyl chloride there was obtained 1-(2,4-dichloro-phenyl)-2-tetrazol-1-yl-vinyl-4-dimethylamino-benzoic acid ester as colourless crystals with m.p. 135° C.

EXAMPLE 15

1-[2-(2,4-Dichloro-phenyl)-2-benzyloxy-vinyl]-1H-tetrazole

Analogously to Example 7a,b, after reacting 1-(2,4-dichlorophenyl)-2-tetrazol-1-yl-ethanone with benzyl chloride there was obtained 1-[2-(2,4-dichloro-phenyl)-2-benzyloxy-vinyl]-1H-tetrazole as colourless crystals with m.p. 92° C.

EXAMPLE 16

1-[2-(2,4-Dichloro-phenyl)-2-isopropoxy-vinyl]-1H-imidazole a) Analogously to Example 1a, after reacting 2,2',4'-trichloroacetophenone with imidazole there was obtained 1-(2,4-dichlorophenyl)-2-(1H-imidazol)-1-yl-ethanone.

b) Analogously to Example 1b, after reacting 1-(2,4-dichlorophenyl)-2-(1H-imidazol)-1-yl-ethanone with isopropyl bromide there was obtained 1-[2-(2,4-dichloro-phenyl)-2-isopropoxy-vinyl]-1H-imidazole, which was isolated as a salt of the composition $C_{14}H_{14}Cl_2N_2O \cdot HCl$ with m.p. 184–186° C.

EXAMPLE 17

1-[2-(2,4-Dichloro-phenyl)-2-butoxy-vinyl]-1H-imidazole

Analogously to Example 16a,b, after reacting 1-(2,4-dichlorophenyl)-2-(1H- imidazol)-1-yl-ethanone with n-butyl bromide there was obtained 1-[2-(2,4-dichloro-phenyl)- 2-butoxy-vinyl]-1H-imidazole, which was isolated as salt of the composition $C_{15}H_{16}Cl_2N_2O \cdot HCl$ with m.p. 205–207° C.

EXAMPLE A

Tablets of the following compositions are produced in the usual manner:

|  | mg/tablet |
|---|---|
| Active ingredient | 100 |
| Powd. lactose | 95 |
| White corn starch | 35 |
| Polyvinylpyrrolidone | 8 |
| Na carboxymethylstarch | 10 |
| Magnesium stearate | 2 |
| Tablet weight | 250 |

EXAMPLE B

Tablets of the following composition are produced in a conventional manner:

|  | mg/tablet |
|---|---|
| Active ingredient | 200 |
| Powd. lactose | 100 |
| White corn starch | 64 |
| Polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/capsule |
|---|---|
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The finished mixture is filled into hard gelatine capsules of suitable size.

What is claimed is:

1. A compound of the formula

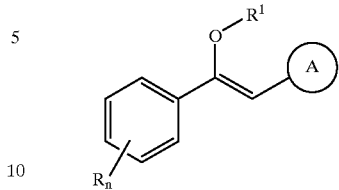

wherein
R is halogen or lower alkyl;
n is 0–3;
$R^1$ is lower alkyl; $C_3$–$C_7$ cycloalkyl; benzyl unsubstituted or substituted by hydroxy, halogen, lower alkoxy or lower alkyl; benzoyl unsubstituted or substituted by amino, lower alkylamino or di-lower alkylamino; acetyl or $C_3$–$C_7$ cycloalkyl-carbonyl; and
A is a tetrazole which is bonded via an N atom;
or a pharmaceutically acceptable salt thereof.

2. A compound of claim 1, wherein n is 1 or 2.

3. A compound of claim 2, wherein R is chlorine.

4. A compound of claim 3, 1-[2-(2,4-dichloro-phenyl)-2-benzyloxy-vinyl]-1H-tetrazole.

5. A compound of claim 3, 2-[2-(4-chloro-phenyl)-2-butoxy-vinyl]-2H-tetrazole.

* * * * *